US008241659B2

(12) United States Patent
Speelmans et al.

(10) Patent No.: US 8,241,659 B2
(45) Date of Patent: *Aug. 14, 2012

(54) NUTRITION WITH LIPIDS AND NON-DIGESTIBLE SACCHARIDES

(75) Inventors: Gelske Speelmans, Wageningen (NL); Martine Sandra Alles, Apeldoorn (NL); Jan Knol, Wageningen (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,753

(22) Filed: Jan. 30, 2012

(65) Prior Publication Data

US 2012/0129935 A1     May 24, 2012

Related U.S. Application Data

(63) Continuation of application No. 11/912,875, filed as application No. PCT/NL2006/050096 on Apr. 21, 2006, now Pat. No. 8,119,155.

(30) Foreign Application Priority Data

Apr. 27, 2005 (EP) .................................. 05103432

(51) Int. Cl.
    *A61K 47/00*     (2006.01)
    *A61K 31/22*     (2006.01)
    *A23L 1/29*     (2006.01)
    *A23L 1/30*     (2006.01)

(52) U.S. Cl. .......................................... 424/439; 514/54

(58) Field of Classification Search ........................ None
See application file for complete search history.

(56) References Cited

U.S. PATENT DOCUMENTS

| | | | | |
|---|---|---|---|---|
| 5,780,451 A | * | 7/1998 | DeMichele et al. | 514/54 |
| 6,489,310 B1 | * | 12/2002 | Brassart et al. | 514/54 |
| 6,994,869 B1 | * | 2/2006 | Bird et al. | 424/439 |
| 7,947,303 B2 | * | 5/2011 | Kessler et al. | 424/439 |
| 2007/0104700 A1 | * | 5/2007 | Garcia-Rodenas et al. | 424/93.45 |
| 2007/0190064 A1 | * | 8/2007 | Speelmans et al. | 424/157.1 |

FOREIGN PATENT DOCUMENTS

| | | | |
|---|---|---|---|
| EP | 1 010 374 | * | 6/2000 |
| EP | 1 010 374 A | | 6/2000 |
| WO | WO 95/26646 | * | 10/1995 |
| WO | WO-95/26646 A1 | | 10/1995 |
| WO | WO 01/02016 | * | 1/2001 |
| WO | WO-01/02016 A | | 1/2001 |
| WO | WO 02/39978 | * | 5/2002 |
| WO | WO-02/39978 A | | 5/2002 |
| WO | WO 2004/000042 | * | 12/2003 |
| WO | WO-2004/000042 A2 | | 12/2003 |
| WO | WO 2004/068969 | * | 8/2004 |
| WO | WO-2004/068969 A1 | | 8/2004 |
| WO | WO 2004/112509 | * | 12/2004 |

OTHER PUBLICATIONS

"Fatty Acids" website:http://replay.waybackmachine.org/20040417120129/http://www.cyberlipid.org/fa/acidOO01.htm; webpage dated Apr. 17, 2004; downloaded Apr. 14, 2011.
21 CFR, subsection 107: Infant Formula; pp. 190-199; (Edition dated Apr. 1, 2003).
Molkentin et al., "Validation of a gas-chromatographic method for the determination of milk fat contents in mixed fats by butyric acid analysis," Eur. J. Lipid Sci. Technol. (2000), pp. 194-201.
US Notice of Allowance in U.S. Appl. No. 11/912,875 dated Oct. 13, 2011.
US Office Action in U.S. Appl. No. 11/912,875 dated Apr. 27, 2011.
US Office Action in U.S. Appl. No. 11/912,875 dated Sep. 15, 2010.
Search Report in International Application No. PCT/NL2006/050096 dated Sep. 29, 2006.

* cited by examiner

*Primary Examiner* — S. Tran
*Assistant Examiner* — Jeffrey T Palenik
(74) *Attorney, Agent, or Firm* — Gilberto M. Villacorta; Sunit Talapatra; Foley & Lardner LLP

(57) ABSTRACT

The invention relates to a liquid nutrition comprising short chain fatty acyl chains and a non-digestible, fermentable saccharide. The composition is particular suitable for use as an infant nutrition. The composition is also suitable for treatment and/or prevention of gut barrier related disorders.

17 Claims, No Drawings

NUTRITION WITH LIPIDS AND NON-DIGESTIBLE SACCHARIDES

CROSS REFERENCE TO RELATED APPLICATIONS

This application is a continuation of U.S. patent application Ser. No. 11/912,875, filed Jul. 8, 2008, which is a national stage application of PCT/NL2006/050096, filed Apr. 21, 2006, and which claims priority to EP 05103432.0 filed Apr. 27, 2005, the entire contents of which are incorporated herein by reference.

TECHNICAL FIELD OF THE INVENTION

The invention relates to a liquid nutritional composition for improving gut barrier function comprising lipids with short chain fatty acyl chains and non-digestible, fermentable saccharides.

BACKGROUND OF THE INVENTION

The gut barrier lines the gastro-intestinal tract and separates the luminal, external part of the body from the systemic, internal part of the body. It protects the body from entering of luminal aggressors, such as antigens, toxins and pathogens. The gut barrier comprises the intestinal epithelium, a continuous monolayer of columnar epithelial cells, the enterocytes, sealed together by protein complexes, such as the tight junctions. A tenuous gut barrier function is found in infants, where the gut has not yet matured sufficiently. Also in malnourished people, patients fasting because of surgery and intensive care patients the gut barrier is disrupted.

Short chain fatty acids stimulate maturation of the gut barrier and maintenance of the gut barrier integrity by serving as an energy source for the enterocytes, stimulating differentiation of the enterocytes and increasing mucus production.

Hence a continuing need exists for a nutritional composition which provide sufficient short chain fatty acids along the gastro-intestinal tract. Such compositions can be advantageously used by infants and patients with an impaired gut function.

WO 02/039978 describes a supplement to be enterally administered for maintaining or restoring the intestinal barrier of the critically ill or chronically ill or people with malnutrition. Said supplement, in the form a solution, contains a) between 15 to 70 g glutamine and/or glutamine precursors, b) at least two representatives from the group of substances acting as antioxidant, and c) short-chain fatty acids and/or precursors of short-chain fatty acids in an amount of from 0.5 to 10 g.

WO 2004/112509 describes a composition for inducing a pattern of gut barrier maturation similar to that observed with breast-feeding and able to improve gut barrier maturation, e.g. during neonatal stress, in particular an infant formula containing a combination of specific ingredients designed to provide a synergistic effect all along gastrointestinal tract on barrier function.

SUMMARY OF THE INVENTION

Nutritional products presently available provide short chain fatty acids insufficiently all along the gastrointestinal tract. Particularly, ingestion of nutritional compositions typically results in high local concentrations of short chain fatty acids, whereas low concentrations of short chain fatty acids are found in other parts of the gastrointestinal tract. The present inventors have recognised this shortcoming of current nutritional formulations.

The present nutritional composition comprises lipids with short chain fatty acids and a non-digestible, fermentable saccharide, preferably a mixture of at least two different non-digestible saccharides. The present composition ensures a sufficient availability of short chain fatty acids in the stomach, duodenum, jejunum, ileum, proximal part of the colon and distal part of the colon, i.e. over the complete length of the gastrointestinal tract.

After ingestion by a monogastric animal (e.g. a human), the short chain fatty acyl chains are released from the present lipids by lipases in the stomach, duodenum, jejunum and proximal ileum. With the release of the short chain fatty acyl chains, short chain fatty acids are provided in the upper part of the gastrointestinal tract. These fatty acids are however absorbed, e.g. by the enterocytes lining the intestinal tract and therefore not available in the lower parts of the gastrointestinal tract. Fermentation of the non-digestible saccharide, and in particular fermentation of a combination of two different non-digestible oligosaccharides, results in the production of short chain fatty acids along the distal ileum, and the proximal and distal part of the colon.

Hence, the present composition provides the beneficial effects of short chain fatty acids, in particular improving gut barrier function, inhibiting growth of gastro-intestinal pathogens, and/or regulating intestinal muscular contractions along the entire length of the gastro-intestinal tract.

The present composition was found to be particularly useful for humans having an impaired or developing gastrointestinal barrier function (e.g. hospital patients and toddlers). In one aspect, the present composition is therefore provided as a nutritional composition suitable for these subjects. When provided as a nutritional composition, the fat fraction therein preferably also contains further fatty acyl chains critical for a good nutritional product, i.e α-linolenic acid (ALA) and linoleic acid (LA).

It was further found that the present composition even further can be improved by combining lipids with short chain fatty acyl chains, indigestible saccharide and long chain poly-unsaturated fatty acids (LC-PUFA), preferably provided by vegetable oil. The PUFA stimulate tight junction formation and thereby reinforce the epithelium surface which is regenerating and maturing as a result of the present lipid and saccharide composition. Hence, the addition of LC-PUFA synergistically stimulates barrier reinforcement.

DETAILED DESCRIPTION OF THE INVENTION

The present invention provides a liquid composition with a viscosity between 1 and 100 mPa·s, comprising at least one source of vegetable oil, at least 0.5 g fat per 100 ml, at least 0.6 wt. % short chain fatty acyl chains based on total fatty acyl chains present and at least 7 wt. % poly-unsaturated fatty acyl chains based on total fatty acyl chains present; and at least 60 mg non-digestible saccharides with a degree of polymerisation (DP) of 2 to 200 per 100 ml, and the use thereof in a method for providing nutrition to an infant.

In a further aspect the present invention provides a method for the prevention and/or treatment in a human subject of allergy, food hypersensitivity, atopic dermatitis, asthma, eczema, gastro-intestinal infections, diarrhoea, intestinal inflammation, intestinal cramps, colics, constipation, bacterial translocation, bacteraemia and/or sepsis, said method comprising administering the present composition to the human subject.

Short Chain Fatty Acids and Short Chain Fatty Acyl Chains.

The term "short chain fatty acids" as used in the present invention refers to aliphatic carboxylic acids with a hydrocarbon chain with one to six carbon atoms. The term "short chain fatty acyl chain" as used in the present invention refers to a short chain fatty acid linked by an ester bond. In a preferred embodiment short chain fatty acid are unbranched fatty acids with two (acetic acid or ethanoic acid), three (propionic acid or n-propanoic acid), four (butyric acid or n-butanoic acid), five (valeric acid or n-pentanoic acid) or six (caproic acid or n-hexanoic acid) carbon atoms.

Lipids Comprising Short Fatty Acyl Chains

Preferably the present composition comprises lipid comprising one or more short chain fatty acyl chains with two to six carbon atoms. In a preferred embodiment the short chain fatty acyl chains as used in the present composition are unbranched, more preferably unbranched and even numbered. Most preferably the present composition comprises the short chain fatty acyl chains comprising two (acetic acid), four (butyric acid) and/or six (caproic acid) carbon atoms. When reference is made to a quantitative amount of the short chain fatty acyl chains, this refers to the quantity of all ester bound short chain fatty acids with a chain length of 1, 2, 3, 4, 5 and 6 carbon atoms, preferably to the quantity of all ester bound short chain fatty acids with a chain length of 2, 4 and 6 carbon atoms.

The lipids comprising fatty acyl chains as preferably used in the present invention are preferably selected from the group consisting of triglycerides, diglycerides, monoglycerides, glycolipids, phospholipids and lysophospholipids. In a preferred embodiment the present composition contains triglycerides comprising short chain fatty acyl chains and/or phospholipids comprising short chain fatty acyl chains, more preferably triglycerides comprising short chain fatty acyl chains. The present triglyceride preferably has at least one short chain fatty acyl chain, which is preferably at the sn-3 position.

Lipids are degraded by lingual, gastric, duodenal (i.e. pancreatic) and small intestinal lipases. Hence, administration of lipids comprising short chain fatty acyl chains results in the release of short chain fatty acids in the stomach, the duodenum, in the jejunum and ileum.

Based on total weight of fatty acyl chains the present composition preferably comprises at least 0.6 wt. % short chain fatty acyl chains, preferably at least 1.2 wt. %, more preferably at least 2.5 wt. %, even more preferably at least 5 wt. %, most preferably at least 10 wt. % based on weight of total fatty acyl chains. In a preferred embodiment the present composition has a wt. % of short chain fatty acyl chains below 50 wt. % based on weight of total fatty acyl chains more preferable below 25 wt. %.

According to a preferred embodiment, the present composition contains between 0.3 and 5 wt. % butyric acid based on based on weight of total fatty acyl chains, preferably between 0.5 and 2.5 wt. %, even more preferably between 0.75 and 2 wt. %. The present composition preferably contains tributyrin (i.e. triglyceride with 3 butyric acid chains attached to the glycerol backbone via ester bonds).

The present composition preferably comprises at least 0.1 wt. % short chain fatty acyl chains based on total dry weight of the composition, more preferably at least 0.25 wt. %, even more preferably at least 0.5 wt. %, most preferably at least 1 wt. %. Preferably, the amount of short chain fatty acyl chains is below 30 wt. %, more preferable below 10 wt. %, even more preferably below 5 wt. % based on dry weight of the composition. The daily dose of short chain fatty acyl chains is preferably at least 2.5 mg per kg body weight, more preferably at least 5 mg per kg body weight, even more preferably at least 10 mg per kg bodyweight, most preferably at least 20 mg per kg body weight. Preferably, the daily dose of short chain fatty acyl chains is below 250 mg per kg body weight, more preferable below 100 mg per kg body weight.

A preferred source of short chain fatty acyl chains are lipids obtained from milk from non-human mammals, preferably cow's milk, goat milk, sheep milk, horse milk, buffalo milk, yak milk, reindeer milk, donkey milk and camel milk, particularly cow's milk and/or goat milk. Milk lipid is sometimes also referred to as milk fat or butter fat. In a preferred embodiment, lipids comprising short chain fatty acyl chains are chemically synthesised from glycerol and short chain fatty acids by enzymes such as esterases. Examples are triacetin and tributyrin. A preferred source of triglycerides comprising short chain fatty acids is Benefat® from Danisco.

Non-Digestible Fermentable Saccharides

The present composition comprises non-digestible, fermentable saccharides (hereinafter referred to as "NDF saccharide") with a DP of 2 to 200. The term "non-digestible saccharides" in the present invention refers to saccharides that remain undigested in the gastrointestinal tract and reach the large intestine unabsorbed, i.e. saccharides that are not digested in the upper intestinal tract of a human, preferably a human infant, e.g. not digested by the acids or enzymes present in the human gastrointestinal tract. For example glucose, fructose, galactose, sucrose, lactose, maltose and maltodextrin are considered digestible. The term "fermentable" as used herein refers to the capability to undergo breakdown by micro-organisms, in the lower part of the gastro-intestinal tract to smaller molecules, in particular to short chain fatty acids and lactate. The fermentability of non-digestible saccharide is preferably determined by the method described in Am. J. Clin. Nutr. 53, 1418-1424 (1991). Preferably the present NDF saccharide is fermentable by Lactobacilli and/or *Bifidobacteria* (see Gibson and Roberfroid, J. Nutr. 125: 1401-1412 (1995). The present NDF saccharide is preferably water-soluble. Water-soluble saccharides are at least 50% water-soluble, according to a method described by L. Prosky et al, J. Assoc. Anal. Chem. 71: 1017-1023, 1988.

Preferably at least 80 wt. %, more preferably at least 95 wt. %, most preferably at least 98 wt. % of the NDF saccharide has a degree of polymerisation (DP) below 100, more preferably below 60, most preferably below 40. The lower DP advantageously reduces viscosity and increases fermentability of the non-digestible saccharides. Preferably at least 50 wt. %, preferably at least 75 wt. % of the NDF saccharide has a DP of 2-8.

The present NDF saccharide is preferably selected from the group consisting of fructo-oligosaccharides, galactooligosaccharides, galactans and fructopolysaccharides, more preferably a galactooligosaccharide, even more preferably a trans-galactooligo-saccharide.

Different Non-Digestible, Fermentable Saccharides

According to a preferred embodiment the present composition contains two different NDF saccharides, i.e. non-digestible saccharide A and non-digestible saccharide B, hereinafter referred to as saccharide A and saccharide B, respectively. The administration of mixtures of saccharides of different sizes, different "classes" and/or "structures" synergistically stimulate the formation of short chain fatty acids, along the distal ileum, and proximal and distal colon, which advantageously influences health.

Saccharide A and saccharide B are different saccharides and have different glycosidic linkages, degree of polymerisation and/or monosaccharide composition. Upon fermentation of these non-digestible saccharides by the gastro-intestinal microflora short chain fatty acids are formed.

The terms saccharide A and saccharide B as used in the present invention preferably refer to mixtures of non-digestible saccharides, rather than to substantially pure saccharides. This is common practice, because the use of saccharides with e.g. one chain length is very expensive. When the saccharide A and/or B are saccharide mixtures, the averages of the respective parameters are used for defining the present invention. For example if saccharide A is a mixture of individual saccharides 25 wt. % Glu-Gal-Gal-Gal, 25 wt. % Glu-Gal-Gal and 50 wt. % Glu-Gal, the average monosaccharide composition is 64% Gal (galactose) and 36% Glu (glucose). The average degree of polymerisation (DP) is (0.25*4+0.25*3+0.5*2=) 2.75.

Monosaccharide Composition

Preferably at least 60%, more preferably at least 95%, more preferably at least 98%, of the total monosaccharide units of saccharide A and B are monosaccharides selected from the group consisting of galactose (gal), fructose (fru) and glucose (glu) monosaccharides. According to a preferred embodiment of the present invention, the percentage of at least one type of monosaccharide in saccharide A is at least 40 mol % higher than the percentage of the same type of monosaccharide in saccharide B, preferably at least 50%, more preferably at least 75%, even more preferably at least 90%. An increased diversity of monosaccharides stimulates an increased and more gradual formation of short chain fatty acids along the distal ileum, the proximal and distal colon.

The percentage of a monosaccharide in the saccharide can simply be calculated by dividing the amount of the respective monosaccharide unit (e.g. glucose) in the saccharide by the total amount of the monosaccharide units in that saccharide and multiply it by 100. When the saccharide is a saccharide mixture, the contribution of each individual saccharide in the saccharide mixture must be taken into account. These percentages in a saccharide mixture can simply be determined by completely hydrolysing the mixture and determining the percentage for each monosaccharide.

For example, in the case where saccharide A is a mixture of glu-(gal)$_{n=2-7}$ with an average monosaccharide composition of 20% glucose and 80% galactose and saccharide B is a mixture of glu-(fru)$_{n=2-7}$ and (fru)$_{n2-7}$ with an average monosaccharide composition of 10% glucose and 90% fructose, the difference in a) glucose is 10%; b) fructose is 90%; and c) galactose 80%. In this example galactose fulfils the criterion that the percentage of at least one monosaccharide selected from the group consisting of glucose, fructose and galactose in saccharide A is at least 40% higher that the percentage of the same monosaccharide in saccharide B.

Preferably saccharide A contains at least 40% galactose, more preferably at least 67% galactose, more preferably at least 75% galactose. Preferably saccharide B contains at least 30% fructose, more preferably at least 67% fructose, even more preferably at least 80% fructose.

Degree of Polymerisation

Saccharides A and B have a degree of polymerisation (DP) of 2 to 200. Preferably at least 80 wt. %, more preferably at least 95 wt. %, most preferably at least 98 wt. % of the cumulative weight of saccharide A and B has a degree of polymerisation (DP) below 100, more preferably below 60, most preferably below 40. The lower DP advantageously reduces viscosity and increases fermentability of the non-digestible saccharides. Preferably at least 50 wt. %, preferably at least 75 wt. % of the cumulative weight of saccharides A and B are non-digestible saccharides with a DP of 2-8. By using a mixture with a high weight percentage of small saccharides the fermentability and stimulation effect on short chain fatty acid production will be increased.

According to a preferred embodiment of the present invention, the DP of saccharide A is at least 5 monosaccharide units lower than the degree of polymerisation of saccharide B, preferably at least 10, even more preferably at least 15. Including a saccharide with an increased degree of polymerisation reduces the osmotic load, which is advantageous for an infant nutrition and improves stimulation of short chain fatty acid formation also at more distal parts of the colon.

Preferably, saccharide A has a DP of 2-15, more preferably 2-8. Preferably saccharide B has DP of 8-100. The saccharides A and B with a different DP may have the same or slightly different monosaccharide composition. When saccharides A and B have different DP and similar monosaccharide composition than the difference in average DP between saccharide A and saccharide B is preferably at least 5, more preferably at least 10, even more preferably at least 15. Preferably, saccharide A and B have a different monosaccharide composition (see above) and a different DP.

For example, if saccharide A is a mixture of glu-(fru)$_{m=2-7}$ and (fru)$_{m=2-6}$ with an average DP of 3.5 monosaccharide units and saccharide B is glu-(fru)$_{n=12-100}$ with an average DP of 25 monosaccharide units; than the difference in the average DP (25−3.5=) 21.5.

Glycosidic Linkage

In a preferred embodiment of the present invention the percentage of at least one glycosidic linkage of saccharide A based on total glycosidic linkages of saccharide A is at least 40% higher the percentage of the same glycosidic linkage in saccharide B, preferably at least 50%, even more preferably at least 75%. The term "glycosidic linkage" as used in the present invention refers to a C—O—C linkage formed between the rings of two cyclic monosaccharides by the elimination of water. An increased diversity in glycosidic linkages stimulates an increased and more gradual formation of short chain fatty acids along the distal ileum, and the proximal and distal colon.

Glycosidic linkages differ in that they covalently bind carbon atoms in the monosaccharide units at differently numbered positions, and/or that they form α or β bonds. Examples of different glycosidic linkages occurring in non-digestible saccharides are β(1,3), α(1,4), β(2,1), α(1,2), and β(1,4) linkages.

Preferably the glycosidic linkages in saccharide A comprises at least 40% β(1,4) and/or β(1,6) glycosidic linkages, more preferably at least 75%. The glycosidic linkages in saccharide B preferably comprise at least 40% β(2,1) glycosidic linkages, more preferably at least 75%.

Combination of Saccharides

In a particularly preferred embodiment, the present saccharide A and B differ in at least two aspects selected from the group of glycosidic linkage, degree of polymerisation and monosaccharide composition. Preferably, the present saccharides A and B differ in degree of polymerisation and in one aspect selected from the group of glycosidic linkage and monosaccharide composition. More preferably, the present saccharide A and B differ in degree of polymerisation and monosaccharide composition. Most preferably all three aspects are different.

Concentration Non-Digestible Saccharide

The present nutritional composition comprises at least 60 mg of NDF saccharide with a DP of 2 to 200 per 100 ml of the present liquid composition, preferably at least 150 mg per 100 ml, more preferably at least 250 mg per 100 ml, even more preferably at least 350 mg per 100 ml. Preferably, the present composition does not contain more than 15 g NDF saccharide with a DP of 2 to 200 per 100 ml, more preferably not more than 10 g per 100 ml, even more preferably not more than 5 g per 100 ml, most preferably not more than 2 g per 100 ml. The present NDF saccharide is preferably administered in a daily dose of 0.1 to 30 g, more preferably 0.5 to 15 g, more preferably 3 to 10 g.

Preferably the present nutritional composition comprises at least 6 mg saccharide A per 100 ml, preferably at least 30 mg/100 ml, even more preferably at least 100 mg/100 ml, most preferably at least 200 mg/100 ml. Preferably the present composition does not contain more than 10 g saccharide A/100 ml, preferably not more than 2 g/100 ml. The present composition preferably comprises at least 6 mg saccharide B per 100 ml, preferably at least 15 mg/100 ml, most preferably at least 30 mg/100 ml. Preferably the present composition does not contain more than 10 g saccharide B per 100 ml, preferably not more than 5 g/100 ml, more preferably not more than 1 g/100 ml.

The weight ratio saccharide A/saccharide B is preferably between 0.01 and 100, more preferably between 0.5 and 100, even more preferably between 4 and 100. A high weight ratio is particularly advantageous when saccharide A has a low DP and saccharide B has a relatively high DP. It ensures an optimal equilibrium between osmolality and fermentability.

Saccharide A and saccharide B preferably comprise between 5 and 100 wt. % based on the total weight of the non-digestible saccharides in the present composition, more preferably 50 to 100 wt. %.

Preferred Saccharides

Non-digestible saccharide A is preferably a saccharide selected from the group consisting of fructo-oligosaccharides, β-galactooligosaccharides, α-galactooligosaccharides and galactans, preferably β-galactooligosaccharides, α-galactooligosaccharides and galactans. According to a more preferred embodiment saccharide A is galactooligosaccharide, more preferably β-galacto-oligosaccharide, even more preferably transgalactooligosaccharide (TOS). Preferably saccharide A comprises β-galactooligosaccharides with β(1, 4) and/or β(1,6) glycosidic bonds and a terminal glucose. TOS is for example commercially available under the tradename Vivinal®GOS (Borculo Domo Ingredients, Zwolle, Netherlands).

Non-digestible saccharide B is preferably a saccharide selected from the group consisting of fructopolysaccharides and fructooligosaccharides, preferably fructopolysaccharide. The terms fructopolysaccharides, polyfructose, polyfructan and fructan are interchangeably used herein and refer to polysaccharides comprising β-linked fructose units, which are preferably linked by β(2,1) and/or β(2,6) glycosidic linkages. Preferably, the fructopolysaccharide contains a terminal β(2,1) glycosidic linked glucose. Preferably, the fructopolysaccharide contains at least 7 β-linked fructose units. In a further preferred embodiment inulin is used as saccharide B. Inulin is a type of fructopolysaccharide wherein at least 75% of the glycosidic linkages are β(2,1) linkages. Typically, inulin has an average chain length between 8 and 60 monosaccharide units. Suitable fructopolysaccharide for use in the compositions is commercially available under the trade name Raftiline®HP (Orafti).

In a further preferred embodiment, saccharide B is a fructooligosaccharide. A fructooligosaccharide is a saccharide comprising β-linked fructose units, which are preferably linked by β(2,1) and/or β(2,6) glycosidic linkages. The fructooligosaccharide preferably contains a β(2,1) glycosidic linked glucose at the reducing end. Preferably, the fructooligosaccharide contains 2 to 6 β-linked fructose units. A suitable source of fructooligosaccharide is Raftilose® (Orafti) or Actilight (Beghin-Meiji).

Polyunsaturated Fatty Acids

PUFA comprise fatty acyl chains with 2 or more double bonds in the acyl chain, such as linoleic acid (LA, a n-6 fatty acid) and α-linolenic acid (ALA a n-3 fatty acid). PUFA, particularly LA and ALA, are essential for subjects with an immature gastrointestinal tract for nutritional reasons, e.g. toddlers and certain hospital patients. Hence the present liquid composition preferably comprises ALA and LA. Preferably the present composition contains PUFA in a sufficient amounts and in a balanced ratio. Hence, the composition comprises at least 7 wt. % PUFA based on total fatty acyl chains, preferably at least 12 wt. %, more preferably at least 15 wt. %, most preferably at least 20 wt. % based on total fatty acyl chains. Preferably the composition does not contain more than 80 wt. % PUFA, preferably not more than 50 wt. % based on total fatty acyl chains.

In order to provide the nutritional requirements, the present composition preferably comprises 0.2 to 2 g LA per 100 ml, and 0.03 to 0.5 g ALA per 100 ml. The weight ratio LA/ALA is preferably between 5 and 15. Preferably, the weight ratio between n-6 and n-3 fatty acids is between 5 and 15.

Long chain polyunsaturated fatty acids (LC-PUFA) were found to reduce the tight junction permeability and so help restore the gut barrier integrity. LC-PUFA also stimulate gut barrier maturation. LC-PUFA are in the body synthesised from polyunsaturated fatty acids (PUFA), such as linoleic acid (LA, a n-6 fatty acid) and α-linolenic acid (ALA a n-3 fatty acid), but the conversion can be at a low rate, especially in infants. The present composition therefore advantageously contains lipids with long chain fatty acyl chains, i.e. with a chain of 20 and/or 22 carbon atoms. Preferably the present composition contains eicosapentaenoic acid (EPA, a n-3 fatty acid), docosahexaenoic acid (DHA, a n-3 fatty acid) and/or arachidonic acid (ARA, a n-6 fatty acid), more preferably ARA and DHA, even more preferably ARA, DHA and EPA.

The content of LC-PUFA with 20 and 22 carbon atoms preferably does not exceed 15 wt. %, preferably does not exceed 10 wt. %, even more preferably does not exceed 5 wt. % of the total weight of fatty acyl chains. Preferably the present composition comprises at least 0.1 wt. %, preferably at least 0.25 wt. %, more preferably at least 0.5 wt. %, even more preferably at least 0.75 wt. % LC-PUFA with 20 and 22 carbon atoms of the total weight of fatty acyl chains. For the same reason, the EPA content preferably does not exceed 5 wt. % of the total fat, more preferably does not exceed 1 wt. %, but is preferably at least 0.05 wt %, more preferably at least 0.1 wt. % of the total fat. The DHA content preferably does not exceed 5 wt. %, more preferably does not exceed 1 wt. %, but is at least 0.1 wt. % of the total fat.

As ARA was found to be particularly effective in reducing tight junction permeability, the present composition comprises relatively high amounts, preferably at least 0.1 wt. %, even more preferably at least 0.25 wt. %, most preferably at least 0.5 wt. % of the total weight of fatty acyl chains. The ARA content preferably does not exceed 5 wt. %, more preferably does not exceed 1 wt. % of the total fat.

In the present ARA containing enteral composition, EPA and DHA are advantageously added to balance the action of ARA, e.g. reduce the potential proinflammatory action of ARA metabolites. Excess metabolites from ARA may cause inflammation. Hence, the present composition preferably comprises ARA, EPA and DHA, wherein the weight ratio ARA/DHA preferably is above 0.25, preferably above 0.5, even more preferably above 1. The ratio is preferably below 25. The weight ratio ARA/EPA is preferably between 1 and 100, more preferably between 5 and 20.

If the present composition is used as an infant formula (e.g. a method for feeding an infant, said method comprising administering the present composition to an infant), the content of LC-PUFA, particularly the LC-PUFA with 20 and 22 carbon atoms, preferably does not exceed 3 wt. % of the total fat content as it is desirable to mimic human milk as closely as possible. For the same reason, the omega-3 LC-PUFA content preferably does not exceed 1 wt. % of the total fat content; the omega-6 LC-PUFA content preferably does not exceed 2 wt. % of the total fat content; the ARA (omega-6) content is preferably below 1 wt. % of the total fat content; and/or the weight ratio EPA/DHA is preferably 1 or lower, more preferably below 0.5.

The LC-PUFA with 20 and 22 carbon atoms may be provided as free fatty acids, in triglyceride form, in phospholipid form, or as a mixture of one or more of the above. The present composition preferably comprises at least one of ARA and DHA in phospholipid form.

For an optimal permeability reduction the present composition preferably has a balanced ratio short chain and long chain fatty acyl chain. Hence, preferably the weight ratio butyric acid/DHA is at least 0.5, preferably at least 1, even more preferably at least 2, even more preferably at least 4. The ratio preferably does not exceed 250.

Fat Source

The present composition is preferably provided in the form of a nutritional composition which is easy to swallow and provides a balanced nutrition. The present composition preferably comprises 20 to 60 en. % fat. The present composition more preferably comprises 30 to 60 en. % fat, even more preferably 35 to 50 en. %, most preferably 39 to 50 en. %. The present composition comprises preferably 15 wt. % to 45 wt. % fat based on dry weight of the composition. The composition preferably comprises at least 0.5 g fat/100 ml, preferably at least 1 g fat/100 ml, more preferably at least 2.5 g fat per 100 ml. Preferably, the composition does not contain more than 10 g fat/100 ml, more preferably not more than 5 g fat per 100 ml. The composition comprises at least one source of vegetable oil, which aims to provide polyunsaturated fatty acids. Preferably, the composition comprises canola oil and/or sunflower oil.

Other Components

The present composition preferably comprises digestible carbohydrate and protein in order to provide energy and/or to support growth and/or support development to the subject in need of the composition. Preferably, the digestible carbohydrate is selected from the group consisting of maltodextrin, starch, lactose, maltose, glucose, fructose, and sucrose. Because lactose is a most important carbohydrate source for infants, the present composition preferably comprises at least 35 wt. % lactose based on weight of total digestible carbohydrate, more preferably at least 50 wt. %, most preferably at least 75 wt. %. Preferably, the composition comprises at least 1 g lactose/100 ml, more preferably at least 2 g/100 ml, even more preferably at least 5 g per 100 ml. The present composition preferably comprises 4 g to 18 g, more preferably 4 to 14 g digestible carbohydrates per 100 ml composition. The present composition preferably comprises 25 to 85 en. % carbohydrate. The present composition more preferably comprises 25 to 75 en. % carbohydrate. The present composition most preferably comprises 40 to 75 en. % carbohydrate. En. % is short for energy percentage and represents the relative amount each constituent contributes to the total caloric value of the preparation. The caloric value is provided by digestible carbohydrates, protein and fat.

The present composition comprises 4 to 20 en. %, more preferably 5 to 16 en. %, most preferably 8 to 12 en. % protein. Preferably the present composition comprises a protein selected from the group consisting of casein, whey, skim milk, and soy protein. The present composition preferably comprises 0.7 g to 7 g, more preferably 0.7 g to 3.5 g protein per 100 ml composition. Preferably, the composition comprises 4 to 20 en. % protein, 20 to 50 en. % fat, and 25 to 85 en. % carbohydrates. More preferably, the composition comprises 4 to 20 en. % protein, 30 to 50 en. % fat, and 25 to 75 en. % carbohydrates.

Preferably, the present composition comprises selenium (Se). Selenium improves the intestinal barrier function and is therefore advantageously added to the present composition in order to improve gut barrier function. Preferably the present composition contains at least 30 ng, more preferably at least 70 ng, even more preferably at least 0.1 µg, most preferably at least 0.15 µg Se per g dry weight of the composition. Preferably, the composition comprises no more than 10 µg, more preferably no more than 1 µg Se per g dry weight of the composition. Preferably the present composition comprises sodium selenite and/or selenomethionine.

Preferably, the present composition comprises zinc (Zn). Zinc protects the intestinal barrier function in the presence of pathogens and plays an important role in enterocyte proliferation. Therefore zinc is advantageously added to the present composition to improve gut barrier function. The present composition preferably contains at least 10 µg zinc per g dry weight of the composition, more preferably at least 30 µg, most preferably at least 50 µg Zn. Preferably, the present composition contains less than 0.3 mg, more preferably no more than 0.2 mg zinc per g dry weight of the present composition. Preferably zinc is added to the composition in the form of zinc sulphate, zinc acetate, zinc chloride, zinc lactate, zinc citrate, zinc gluconate and/or zinc oxide.

Preferably, the present composition comprises vitamin A and/or its precursor β-carotene. This vitamin is essential for epithelial cell growth, differentiation and proliferation and is therefore advantageously added to the present composition to improve gut barrier function. Preferably, at least 4 µg retinol equivalent (RE) per g dry weight of the composition, more preferably at least 6 µg retinol equivalent (RE) is present. Preferably the present composition contains less than 20 µg RE per g dry weight of the present composition.

The present compositions preferably comprise minerals, trace elements and vitamins, choline, taurine, carnitine, myo-inositol and/or mixtures thereof. Preferably the present composition contains taurine, which represses the damage to enterocytes caused by inflammation. Thus taurine is advantageously added to the present composition. Preferably the present composition contains at least 3 mg, more preferably at least 6 mg, most preferably at least 10 mg taurine per 100 ml.

Liquid Composition

Stool irregularities (e.g. hard stools, insufficient stool volume, diarrhoea) are a major problem in many infants and ill subjects who receive liquid foods. Therefore, the present liquid composition preferably has an osmolality between 50 and 500 mOsm/kg, more preferably between 100 and 400 mOsm/kg.

It is also important that the present liquid composition does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

The present liquid composition has a viscosity between 1 and 100 mPa·s, preferably between 1 and 60 mPa·s, more preferably between 1 and 20 mPa·s, most preferably between 1 and 10 mPa·s. The low viscosity ensures a proper administration of the liquid, e.g. a proper passage through the whole of a nipple.

The present composition is preferably prepared by admixing a powdered composition comprising with water. Normally infant formula is prepared in such way. The present invention thus also relates to a packaged power composition wherein said package is provided with instruction to admix the powder with a suitable amount of liquid, thereby resulting in a liquid composition with a viscosity between 1 and 100 mPa·s. This viscosity closely resembles the viscosity of human milk. Furthermore, a low viscosity results in a normal gastric emptying and a better energy intake, which is essential for infants which need the energy for optimal growth and development. The viscosity of the present liquid can be suitably determined using a Physica Rheometer MCR 300 (Physica Messtechnik GmbH, Ostfilden, Germany) at shear rate of 95 $s^{-1}$ at 20° C.

Applications

The composition according to the present invention has been found to be particularly useful as an infant nutrition. Hence the present invention provides a method for providing nutrition to a human infant, said method comprising administering the present liquid composition to an infant.

Preferably the infant has an age between 0 and 48 month, more preferably between 0 and 36 month, most preferably between 11 and 36 months, e.g. a toddler.

Since short chain fatty acids are an important energy source for enterocytes and stimulate differentiation of enterocytes, the present composition can be advantageously used to restore, maintain and/or maturate the intestinal barrier function along the entire gastrointestinal tract in a human. The present composition can thus suitably be used to treat and prevent diseases wherein an impaired intestinal barrier function plays an (important) role. The present liquid composition is especially suitable to treat and/or prevent allergy, food hypersensitivity, atopic dermatitis, eczema, gastro-intestinal infections, diarrhoea and/or intestinal inflammation in infants, by orally administering the present composition. Since short chain fatty acids also play an important role in intestinal neuro-muscular behaviour, the composition is especially suitable to prevent and/or treat cramps, colics and/or constipation. The reduced occurrence of these diseases is due to the optimised short chain fatty acid production along the entire length of the gastro-intestinal tract.

Other patients suffering from a decreased intestinal barrier function can also advantageously use the present composition. Hence, the present composition can also be advantageously used to treat and/or prevent diarrhoea, bacterial translocation, bacteraemia, sepsis, malnourishment, and/or intestinal inflammation. The present composition can also be suitably used by patients undergoing surgery, patients undergoing anticancer therapy and patients suffering from injuries caused by heat, friction, electricity, radiation, or chemicals. The present composition is preferably administered orally. The composition is also particular suitable for administration via a tube or through a straw.

EXAMPLES

Example 1

Digested Short Chain Triglycerides Inhibits Pathogenic Bacteria in the Small Intestine Tributyrin (Aldrich) was incubated at a concentration of 33 mM at 37° C. for 90 minutes under anaerobic conditions in medium representing the stomach (8.3 g/l bacteriological peptone, 3.1 g/l NaCl, 0.11 g/l $CaCl_2$, 1.1 g/l KCl, 0.6 g/l $KH_2PO_4$, 1.0 g/l glucose, pH 3.0, 22.2 mg/l pepsin, (from porcine stomach mucosa; Sigma P-6887), and 22.2 mg/l lipase (Rhizopus F-AP15; Amano Pharmaceuticals)). As a control an incubation without tributyrin was performed. After the incubation a tenfold dilution of this suspension was made into medium representing the small intestine (5.7 g/l bacteriological peptone, 1.25 g/l NaCl, 0.055 g/l $CaCl_2$, 0.15 g/l KCl, 0.68 g/l $KH_2PO_4$, 1.0 g/l $NaHCO_3$ 0.3 g/l $Na_2HPO_4$, 0.7 g/l glucose, pH 6.5, 20.3 g/l pancreatin (pig pancreatin; Sigma P-1750) and 5.5 g/l bile (bovine bile; Sigma B-3883)). Intestinal (opportunistic) pathogens were grown overnight in BHI broth (Oxoid) and washed and concentrated 3× in small intestinal medium. At t=0 the microtiter wells filled with the small intestinal medium with or without digested tributyrin were inoculated in triplicate with the pathogens (20 μl added to 250 μl medium). At time points 105 and 210 minutes 100 μl samples were taken. Threefold dilution series were made in PBS (Gibco) for each pathogen and 5 μl of each dilution was spotted in duplo on a square BHI-plate by using a template. The spotted plates were dried and anaerobically incubated for 48 hours at 37° C. By comparing the results of the incubation with tributyrin with those of the control without tributyrin the percentage inhibiting effect of hydrolysed tributyrin was calculated. The results are shown in table 1. The growth of *Bifidobacteria* or lactic acid bacteria was not inhibited in the presence of 10 mM butyrate (data not shown).

TABLE 1

| Percentage inhibition by hydrolysed tributyrin | | |
|---|---|---|
| Strain | T = 105 min | T = 210 min |
| *Shigella flexneri* LMG10472 | 49.4 | 55.9 |
| *Staphylococcus aureus* LMG10147 | 83.0 | 91.6 |
| *Staphylocoocus epidermidis* LMG10273 | 0 | 29.8 |
| *Klebsiella pneumoniae*, clinical isolate | 44.8 | 45.1 |
| *Clostridium difficile*, clinical isolate | 92.6 | 97.0 |
| *Streptococcus agalactica* LMG14694 | 100 | 100 |
| *Yersinia enterocolitica* LMG67899 | 0 | 50.4 |

These results demonstrate that short chain triglycerides upon digestion by lipases exert a bactericidal or growth inhibitory effect on some common gut pathogens in the small intestine.

Example 2

Organic Acids Formed Upon Colonic Fermentation Inhibit Growth of Pathogenic Bacteria Pathogenic bacteria were grown overnight on Tryptic Soy Broth (Oxoid) at 37° C., and inoculated into Tryptic Soy Broth (5 μl added to 250 μl in wells of a microtiter plate) with either pH 7.0, representing the pH of the colon of infants fed a standard infant formula or pH 5.5, representing the pH of the colon of infants fed an infant formula supplemented with 0.4 g/l galacto-oligosaccharides (from Vivinal Gos) and polyfructose (raftilinHP) in a weight ratio of 9/1 and comprising concentrations of organic acids as observed in feces of these infants. As a control, no organic acids were added. Growth at 37° C. was monitored by measuring the turbidity ($OD_{600}$).

The results are shown in Table 2. It can be concluded that the physiological changes (i.e. a lowering of the pH combined with the presence of organic acids) in the colon induced by fermentation of non-digestible saccharides inhibit the growth of pathogenic bacteria. The growth of *Bifidobacteria* and lactic acid bacteria was not inhibited (data not shown).

TABLE 2

Growth inhibition by organic acids and low pH

| Strain | No acids pH 5.5 | pH 7.0 | organic acids[a] pH 5.5 | pH 7.0 |
|---|---|---|---|---|
| *Escherichia coli* ATCC35401 | _[b] | 0 | --- | -- |
| *Salmonella typhimurium* LMG22714 | - | 0 | --- | --- |
| *Klebsiella pneumoniae* clinical isolate | - | 0 | --- | 0 |
| *Staphylococcus aureus* LMG10147 | - | 0 | --- | -- |
| *Enterococcus faecalis* LMG11396 | 0 | 0 | --- | - |

[a]organic acids: 75 mM acetate, 20 mM propionate, 7.5 mm butyrate, 47.5 mM lactate or 100 mm acetate
[b]0: no growth inhibition
-: weak growth inhibition (5 to 20%) compared to pH 7.0 with no acids
--: medium growth inhibition (20 to 60%) compared to pH 7.0 with no acids
---: strong growth inhibition: (60 to 100 %) compared to pH 7.0 with no acids From the results shown in example 1 and 2 it can be concluded that upon oral administration of a composition comprising short chain triglycerides and a non-digestible saccharide, short chain fatty acids are released and having antipathogenic effects in the small intestine and the colon.

Example 3

Prolonged Release of Short Chain Fatty Acids

Micro-organisms were obtained from fresh feces from bottle fed babies. Fresh fecal material from babies ranging 1 to 4 months of age was pooled and put into preservative medium within 2 h.

Substrates for fermentation were the following prebiotics:

| 1 | 85 mg TOS (from Vivinal GOS) |
| 2 | 76.5 mg TOS (from Vivinal GOS) and 8.5 mg inulin (from raftilin HP) 9/1 (w fibre/w fibre) |
| 3 | 85 mg Inulin (raftilin HP) |
| 4 | none (blanc). |

McBain & MacFarlane medium: Buffered peptone water 3.0 g/l, yeast extract 2.5 g/l, mucin (brush borders) 0.8 g/l, tryptone 3.0 g/l, L-Cysteine-HCl 0.4 g/l, bile salts 0.05 g/l, $K_2HPO_4.3H_2O$ 2.6 g/l, $NaHCO_3$ 0.2 g/l, NaCl 4.5 g/l, $MgSO_4.7H_2O$ 0.5 g/l, $CaCl_2$ 0.228 g/l, $FeSO_4.7H2O$ 0.005 g/l. 500 ml Scott bottles are filled with the medium and sterilised for 15 minutes at 121° C.

Buffered medium: $K_2HPO_4.3H_2O$ 2.6 g/l, $NaHCO_3$ 0.2 g/l, NaCl 4.5 g/l, $MgSO_4.7H_2O$, 0.5 g/l, $CaCl_2$ 0.228 g/l, $FeSO_4.7H_2O$ 0.005 g/l. Adjust to pH 6.3±0.1 with $K_2HPO_4$ or $NaHCO_3$. 500 ml Scott bottles are filled with the medium and sterilised for 15 minutes at 121° C.

Preservative medium: Buffered peptone 20.0 g/l, L-Cysteine-HCl 0.5 g/l, Sodium thioglycollate 0.5 g/l, resazurine tablet 1 per litre, adjust to pH 6.7±0.1 with 1 M NaOH or HCl. Medium is boiled in microwave. 30 ml serum bottles are filled with 25 ml medium and sterilised for 15 minutes at 121° C.

The fresh feces are mixed with the preservative medium and can be preserved in this form for several hours at 4° C.

Fecal suspension: The preserved solution of feces was centrifuged at 13,000 rpm for 15 minutes. The supernatant was removed and the feces was mixed with the McBain & Mac Farlane medium in a weight ratio of 1:5.

3.0 ml of the fecal suspension were combined with 85 mg prebiotic or with no addition (blanc) in a bottle and mixed thoroughly. At t=0 a sample was withdrawn (0.5 ml). 2.5 ml of the resulting suspension was brought in a dialysis tube in a 60 ml bottle filled with 60 ml of the buffered medium. The bottle was closed well and incubated at 37° C. Samples were taken from the dialysis tube (0.2 ml) or from the dialysis buffer (1.0 ml) with a hypodermic syringe after 3, 24, and 48 hours and immediately put on ice to stop fermentation.

The short chain fatty acids (SCFA) acetic, propionic, and n-butyric were quantitatively determined by a Varian 3800 gas chromatograph (GC) (Varian Inc., Walnut Creek, U.S.A.) equipped with a flame ionisation detector. 0.5 µl of the sample was injected at 80° C. in the column (Stabilwax, 15×0.53 mm, film thickness 1.00 µm, Restek Co., U.S.A.) using helium as a carrier gas (3.0 psi). After injection of the sample, the oven was heated to 160° C. at a speed of 16° C./min, followed by heating to 220° C. at a speed of 20° C./min and finally maintained at a temperature of 220° C. for 1.5 minutes. The temperature of the injector and detector was 200° C. 2-ethylbytyric acid was used as an internal standard. Values were corrected for blanc.

Results are shown in Table 3. Table 3 shows that fermentation of the mixture of TOS/Inulin HP results in a significantly higher amount of SCFA per g fibre than the single components.

Table 4 shows the kinetics of SCFA formation. In the first 3 h the highest amount of SCFA is formed with the mixture of prebiotics. A fast fermentation at the beginning of the colon is of importance because of antipathogenic effects.

The combination of TOS/inulin HP also shows a higher SCFA formation between 24 and 48 h compared to the single components, indicating that in the distal part of the colon still SCFA is formed which has a beneficial effect on colon permeability, gut barrier integrity, mucus formation and antipathogenic effects.

The high quantity of short chain fatty acids (Table 3) is indicative for the sufficient provision of short chain fatty acids in the lower parts of the gastrointestinal tract. The increased quantity of short chain fatty acids in the 24-48 time interval is indicative for a relatively increased quantity of short chain fatty acids in the distal parts of the lower gastrointestinal tract. Both measures are indicative for the suitability of combining the non-digestible fermentable oligosaccharides with the present short chain fatty acyl chains. These results are indicative for the beneficial effects of the non-digestible fermentable oligosaccharides, particularly the galactooligosaccharides (TOS), and especially the combination long and short oligosaccharides with a different structure (TOS/Inulin HP).

TABLE 3

SCFA formation in infant faeces (mmol per g prebiotic) blanc corrected, after 48 *in vitro* fermentation

| | SCFA (mmol/g prebiotic) | | | |
|---|---|---|---|---|
| Prebiotics | acetate | propionate | butyrate | Total SCFA |
| TOS | 2.95 | 1.05 | 0.16 | 4.16 |
| TOS/inulin HP | 3.71 | 1.03 | 0.18 | 4.92 |
| Inulin HP | 1.60 | 0.29 | 1.03 | 2.92 |

TABLE 4 kinetics of total SCFA formation in infant faeces
(mmol/g prebiotic) (blanc corrected)

| Prebiotics | Time interval (hours) | | |
|---|---|---|---|
| | 0-3 hrs | 3-24 hrs | 24-48 hrs |
| TOS | 0.23 | 3.85 | 0.13 |
| TOS/inulin HP | 0.40 | 4.49 | 0.24 |
| Inulin HP | 0.00 | 3.05 | 0.05 |

From the results shown in example 1 and 2 it can be concluded that upon oral administration of a composition comprising short chain triglycerides and a mixture of two different non-digestible saccharides, short chain fatty acids are released and having anti-pathogenic effects in the small intestine and, the proximal part of the colon and the distal part of the colon.

Example 4

Infant Nutrition

A drink, comprising per 100 ml 67 kcal and
1.9 g protein: (11.3 en. %; cow's milk protein)
3.0 g fat: (40.3 en. %; 0.75 g milk fat; 1.95 g high oleic sunflower oil/canola oil mixture; 0.3 g corn oil)
8.11 g digestible carbohydrates: (48.4 en. %; 7.8 g lactose, 0.22 glucose; 0.01 galactose; 0.01 polysaccharides; 0.06 organic acids)
0.8 g fibre: (0.72 g transgalactooligosaccharides (from Vivinal® GOS, Borculo Ingredients, the Netherlands); 0.08 g long chain inulin (from Raftilin HP, Orafti, Belgium)).
micronutrients: 0.89 mg zinc; 2.3 μg Se; 65 μg-RE vitamin A of which 24.6 μg-RE β-carotene; 10 mg choline
osmolality: 355 osmol/kg
viscosity: 3 mPa·s
Fatty acyl chain (fatty acid) composition in g per 100 g fatty acyl chains:

| C-4:0 (butyric) | 0.87 | C-6:0 (caproic) | 0.50 |
|---|---|---|---|
| C-8:0 | 0.37 | C-10:0 | 0.75 |
| C-12:0 | 0.99 | C-14:0 | 2.86 |
| C-16:0 | 11.69 | C-16:1n7 | 0.77 |
| C-17:0 | 0.01 | C-18:0 | 4.36 |
| C-18:1n9 | 46.81 | C-18:2n6 (linoleic) | 21.74 |
| C-18:3n3 (α linolenic) | 3.57 | C-18:3n6 | 0.07 |
| C-20:0 | 0.34 | C-20:1n9 | 0.76 |
| C-22:0 | 0.29 | C-22:1n9 | 0.11 |
| C-24:1n9 | 0.07 | | |

The invention claimed is:

1. An infant formula composition comprising between about 0.3 and 5 wt % of butyric acid based on total fatty acyl chains in the composition.

2. The composition of claim 1, comprising 4 to 20 en. % protein, 30 to 50 en. % fat, and 25 to 75 en. % carbohydrates.

3. The composition of claim 1, comprising at least 7 wt. % polyunsaturated fatty acyl chains based on total fatty acyl chains.

4. The composition of claim 1, comprising at least 60 mg non-digestible saccharides with a degree of polymerisation of 2 to 200 per 100 ml.

5. The composition of claim 1, further comprising galacto-oligosaccharides.

6. The composition of claim 1, wherein the composition is a liquid.

7. The composition of claim 1, having a viscosity between 1 and 100 mPa·s.

8. The composition of claim 6, further comprising at least 1 g lactose per 100 ml liquid composition.

9. The composition of claim 6, comprising at least 0.5 g fat per 100 ml liquid composition.

10. The composition of claim 9, comprising at least 1 g fat per 100 ml liquid composition.

11. The composition of claim 1, comprising at least two different non-digestible saccharides A and B, wherein:
  (a) non-digestible saccharide A has a degree of polymerisation of 2 to 200;
  (b) non-digestible saccharide B has a degree of polymerisation of 2 to 200; and wherein
    (i) the percentage of at least one type of monosaccharide in saccharide A is at least 40 mol % higher that the percentage of the same type of monosaccharide in saccharide B;
    (ii) percentage of at least one type of glycosidic linkage of saccharide A based on total glycosidic linkages of saccharide A is at least 40% higher the percentage of the same type of glycosidic linkage in saccharide B; and/or
    (iii) the degree of polymerisation of saccharide A is at least 5 monosaccharide units lower than the degree of polymerisation of saccharide B.

12. The composition of claim 10, wherein non-digestible saccharide A is β-galactooligosaccharide and saccharide B is a non-digestible saccharide selected from the group consisting of fructopolysaccharides and fructooligosaccharides.

13. The composition according to claim 1, further comprising eicosapentaenoic acid, arachidonic acid and/or docosahexaenoic acid.

14. A method for treatment of allergy, food hypersensitivity, atopic dermatitis, asthma, eczema, gastro-intestinal infections, diarrhea, intestinal inflammation, intestinal cramps, colics, constipation, bacterial translocation, bacteraemia and/or sepsis in a human subject, the method comprising administering to the human subject an infant formula composition comprising between about 0.3 and 5 wt % of butyric acid based on total fatty acyl chains in the composition.

15. The method according to claim 14 for the treatment of gastro-intestinal infections, diarrhea, intestinal inflammation, intestinal cramps, colics, and/or constipation.

16. The method according to claim 14, wherein the human subject is an infant.

17. A method for providing nutrition to an infant, the method comprising administering to the infant an infant formula composition comprising between about 0.3 and 5 wt % of butyric acid based on total fatty acyl chains in the composition.

* * * * *